United States Patent [19]

Takahashi et al.

[11] Patent Number: 4,954,723
[45] Date of Patent: Sep. 4, 1990

[54] DISK SURFACE INSPECTION METHOD AND APPARATUS THEREFOR

[75] Inventors: Ippei Takahashi; Takeshi Wakita, both of Shizuoka, Japan

[73] Assignee: Fuji Photo Film Co., Ltd., Kanagawa, Japan

[21] Appl. No.: 372,632

[22] Filed: Jun. 13, 1989

[30] Foreign Application Priority Data

Jun. 13, 1988 [JP] Japan .................. 63-145356

[51] Int. Cl.⁵ ............................ G01N 21/89
[52] U.S. Cl. .................. 250/572; 250/563; 356/237; 356/446
[58] Field of Search ............ 250/572, 562, 563; 356/237, 446, 448, 430, 432

[56] References Cited

U.S. PATENT DOCUMENTS 4,464,050 8/1984 Kato et al. .................. 250/572
4,598,997 7/1986 Steigmeier et al. ............ 250/572
4,794,264 12/1988 Quackenbos et al. ........... 356/237

FOREIGN PATENT DOCUMENTS 55-87907 7/1980 Japan .

Primary Examiner—Edward P. Westin
Attorney, Agent, or Firm—Young & Thompson

[57] ABSTRACT

A method and apparatus for scanning a surface of an optical disk which has signal recording pits or bumps covered with a transparent layer, with a flying spot to detect surface defects of the optical disk surface. The optical disk is rotated at a constant speed of rotation and scanned along a scanning line parallel to but spaced at least 10 mm from a line radial to the center of rotation of the optical disk. A light-detecting unit receives diffused light reflected by the disk surface to provide an output corresponding to the intensity of the diffused light and converts it into an electric output which is used to evaluate the surface of the optical disk.

4 Claims, 5 Drawing Sheets

DISK SURFACE INSPECTION METHOD AND APPARATUS THEREFOR

BACKGROUND OF THE INVENTION

The present invention relates to a method and apparatus for optically inspecting a surface of a disk, and more particularly to a method and apparatus for optically detecting surface defects of a disk, such as scratches or pin holes.

Conventionally, a surface of a disk, such as a laser visual disk (which is hereinafter referred to as an LVD) or a compact disk (which is hereinafter referred to as a CD), is visually inspected and evaluated. Because of the dependency of the accuracy of visual inspection on the inspector's ability and of the low efficiency of visual inspection, much effort has been put into the development of automatic inspection technology for LVDs and CDs for many years.

To automatically detect surface defects of, for example, a long web, the web is continuously transported lengthwise in one direction at a constant speed and scanned with a flying spot in a direction perpendicular to the direction in which the web is transported. Light modulated and reflected by the surface of the web including surface defects is measured by means of a light-detecting device to detect surface defects, thereby evaluating the surface of the web. Such a method is described in, for example, Japanese Unexam. Pat. Publ. No. 55-87907. Because it is a noncontact method, it is basically effectively applicable in inspecting LVDs and CDs.

Meanwhile, optical disks, such as LVDs, have a signal recording surface that is formed thereon with a great number of pits or bumps and covered with a transparent protective layer. These pits or bumps are distributed on coaxial tracks at regular spacings. Light diffracted and reflected by the pit is detected to read a signal recorded on the recording surface of the disk. Pit configurations and arrangements are classified into two groups according to how the disks are driven to record and reproduce signals, namely the types of disk drive systems, which are a constant linear velocity (CLV) system and a constant angular velocity (CAV) system. In the CLV type of LVDs which are driven so that all tracks run at a constant and same linear velocity, the pits are formed in a same configuration and arranged at regular circumferential spacings for all tracks. On the other hand, in the CAV type of LVDs which are always driven at a constant velocity independently of the positions of the tracks, pits on a track are formed so as to be shorter in circumferential length than those on a track located outwardly of the track and are arranged more closely than those on the other track.

One such conventional surface defect inspection apparatus that scans a surface of an LVD with a flying spot is shown in FIG. A scanning beam 3 generated by a scanner 2 scans a surface of an LVD 4 along a line 5 disposed radially of the center of rotation 6 of the LVD 4. The light 3a reflected directly from the surface of the LVD 4 is received by a light-detecting unit 7 and converted into a photoelectric output thereby. The photoelectric output is analyzed to evaluate the surface of the LVD 4. Because of the uniformity of surface reflectance over the surface of the LVD 4 to be inspected, if the scanning line 5 is disposed radially of the center of rotation 6 of the LVD, the reflected light 3a from the rotating LVD has no fluctuations. If the scanning beam 3 passing through a transparent protective layer 8 coated over the LVD 4 is diffracted and diffused by the pits of the LVD 4, the rays diffracted and diffused by the pits usually travel in directions greatly different from that in which the reflected light 3a from the surface of the transparent layer 8 of the LVD 4 travels and so are not received by the light-detecting unit 7.

If the light-detecting unit 7 receives not only diffused rays 3b reflected by a surface defect S of the LVD 4 but also diffracted and diffused rays 11 reflected by the pit 10a of the LVD 4 as shown in FIG. 2, because, in the CLV type of LVDs, the light 11 diffused and reflected by the respective pit 10a is directed toward the light-detecting unit 7 at the same angle as the light diffused and reflected by the surface of the LVD 4, the light-detecting unit 7 will receive the diffracted and diffused light 11, which is undesirable to evaluate the surface of the LVD 4, as well as the reflected light 3a.

Because the amount or intensity of the light diffused by each pit is substantially constant independently of its location on the CLV type LVD, the light-detecting unit 7 can easily separate the diffused light 11 reflected by the pits 10a from those reflected by the surface defect S. In the CAV type LVD, because the pits on different tracks are different in size and distributed at different angular spacings, angles at which the light rays diffused and reflected by the pits on the different tracks are oriented are different according to the locations of the tracks. On the other hand, the angle of reflection of the diffused light from the surface of the LVD 4 is substantially constant over the surface of the LVD 4. The light-detecting unit 7, which has an effective light-detecting area having a width W (shown by a dotted line in FIG. 3), receives the diffused light 11 in the form of a circular arc reflected from the pits on different tracks at different locations thereof and misses them partly as is shown in FIG. 3. That is, as is shown in FIG. 4, the farther radially inward is the track on which a pit is located, the lower will be the photoelectric output from the light-detecting unit 7 receiving the diffused light from the pit. The change or difference of output from the light-detecting unit 7 due to the locations of the pits is considerably greater than that due to surface defects of the LVD 4. Therefore, it is quite difficult to electrically compensate such changes caused by the locations of pits and, accordingly, the conventional surface inspection method and apparatus is not always effectively applicable to LVDs.

OBJECT OF THE INVENTION

It is, therefore, an object of the present invention to provide a method and apparatus for inspecting a surface of a compact disk based on diffused and reflected light from the surface in which the accuracy of inspection is independent of diffused light from pits or bumps for recording which are covered by a transparent layer.

SUMMARY OF THE INVENTION

The above object of the present invention is achieved by a method of surface inspection and apparatus therefor in which a disk surface is scanned with a light beam along a scanning line parallel to but spaced from a line extending radially of the center of rotation of the disk under inspection. This method and apparatus is more effectively applied to a laser visual disk (LVD) formed with a signal recording surface comprising a coaxial arrangement of pits or bumps which are covered and protected by a transparent layer.

In accordance with a preferred embodiment of the present invention, the distance by which the scanning line is spaced from the radial line of the LVD is preferably greater than 10mm.

The surface inspection apparatus in accordance with the present invention comprises a scanner for scanning a surface of a disk in rotation, along a scanning line parallel to but spaced from a line extending radially of the center of rotation of the disk, and light-detecting means for receiving diffused light reflected by the disk surface to provide an electric output corresponding to the intensity of the diffused light. Level setting means is provided in association with the light-detecting means so as to establish a level for inspection according to fluctuations or changes of low-frequency component of the electric output. Abnormal output component detecting means is provided in association with the light-detecting means for comparing the electric output with the level established so as to detect abnormal components of the electric output from the light-detecting means, thereby detecting the presence of surface defects.

Because of the scanning line being spaced from a line radial to the center of rotation of the disk, the surface inspection can be effected without the influence of light diffracted and diffused by pits or bumps of the disk covered with the transparent layer, so that surface defects of the disk can be effectively detected. A 10mm separation of the scanning line from the radial line enables inspecting the surface of an LVD disk with a high accuracy.

DETAILED DESCRIPTION OF THE INVENTION

Figure 1:
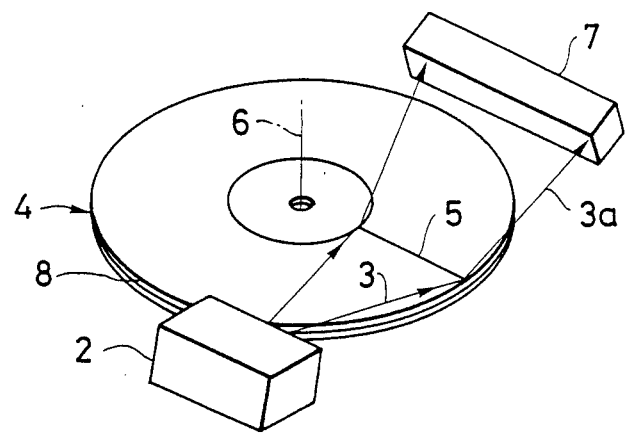
FIG. 1 is an explanatory perspective view showing a conventional LVD surface inspection apparatus.
Figure 2:
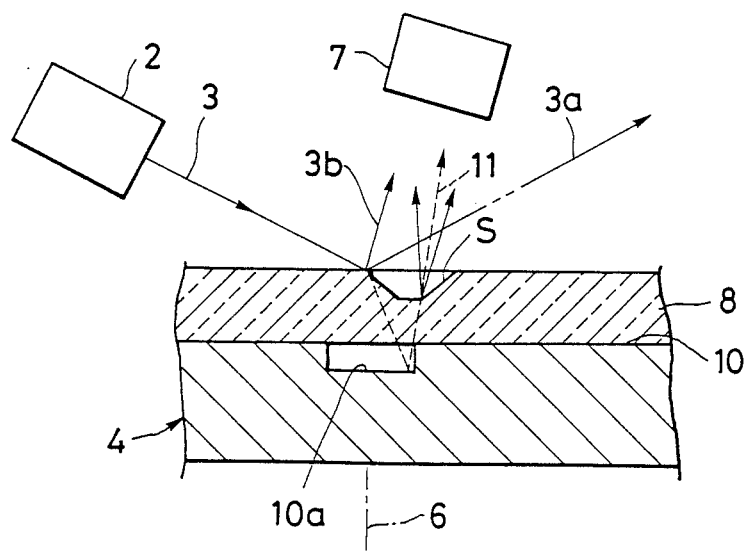
FIG. 2 is an illustration showing a reflection pattern of light from an LVD.
Figure 3:
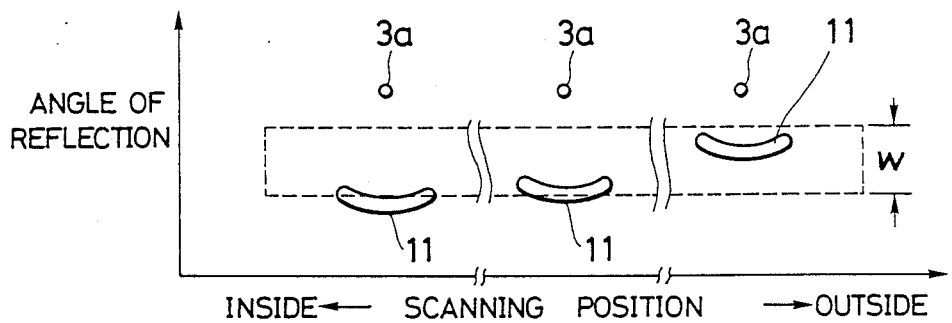
FIG. 3 is an illustration showing a pattern of light reflected from an LVD surface onto a light-detecting unit.
Figure 4:
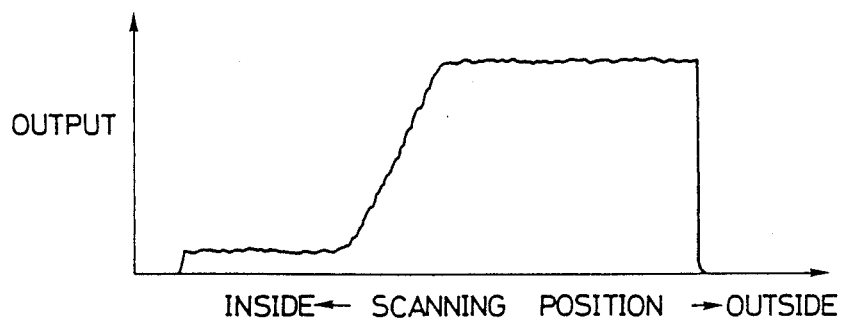
FIG. 4 is a graph showing a waveform of a photoelectric output from a light-detecting unit receiving light reflected by the surface of an LVD with no surface defect.
Figure 5:
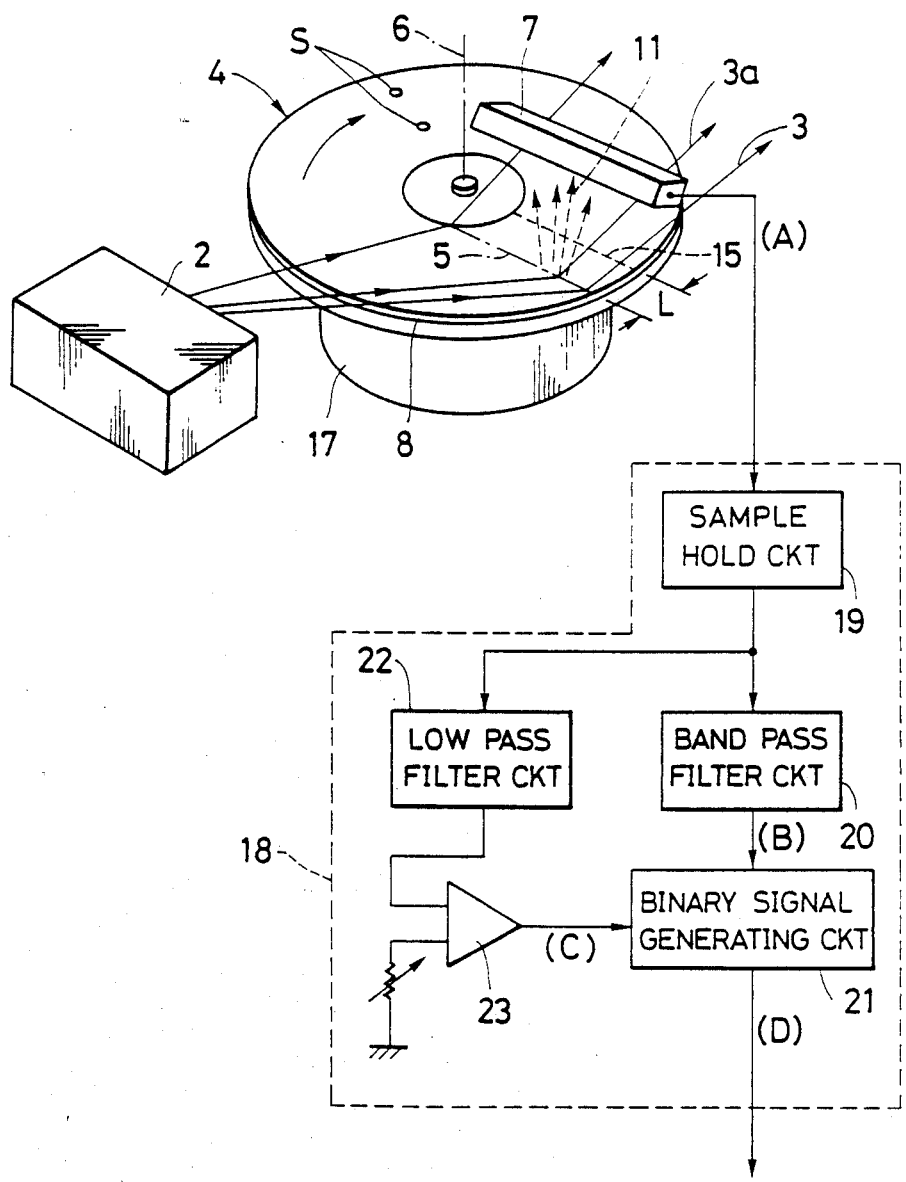
FIG. 5 is an explanatory perspective view, partly in block diagram, showing a surface inspection apparatus in accordance with a preferred embodiment of the present invention.
Figure 6:
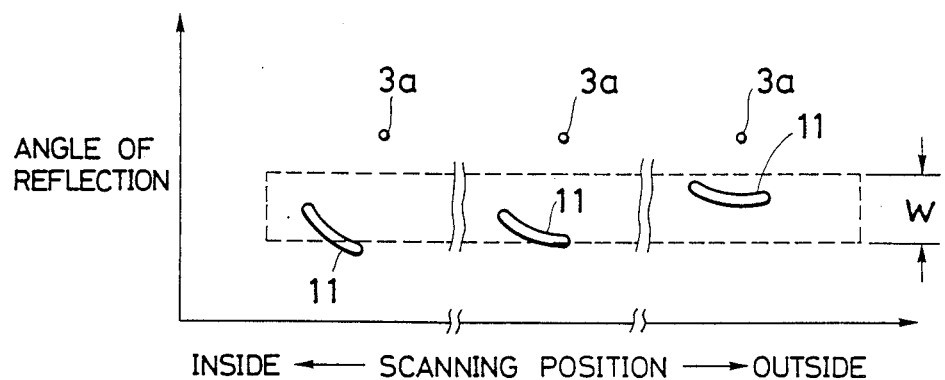
FIG. 6 is an illustration similar to FIG. 3, showing a pattern of light reflected from an LVD surface onto a light-detecting unit of the surface inspection apparatus shown in FIG. 5.

Referring now to the drawings, and first to FIG. 5, a surface inspection apparatus in accordance with a preferred embodiment of the present invention is shown, having a scanner 2 consisting of a laser oscillator and a polygonal rotary mirror, which is well known in the art for forming a flying spot and therefore need not be explained here in detail. The scanner 2 forms a laser beam 3 which scans the upper surface of a CAV type LVD 4 under inspection along a line 5 spaced a distance L from and parallel to a line 15 which is radial to the center of rotation of the LVD 4. The distance L is ordinarily greater than 10mm. The LVD 4 is driven in rotation about its axis 6 by a disk drive 17 at a constant speed, so that the laser beam 3 can scan all the surface of the LVD 4, or at least that portion which is spaced more than a predetermined distance from axis 6.

A light-detecting unit 7 is so disposed above the LVD 4 and parallel to the lines 5 and 15 as to receive diffused light reflected from surface defects S of the LVD 4, and light diffracted and diffused by pits of the LVD 4. If the surface of the LVD 4 has no surface defects S, the reflected light 3a from the surface is directed at a regular angle so as not to be received by the light-detecting unit 7.

When the light-detecting unit 7 receives light, it produces an output of a level corresponding to the intensity of the received light and sends the output to a surface defect detection unit 18. This surface defect detection unit 18 comprises a sample hold circuit 19 for waveform-shaping the output at a predetermined sampling frequency, a band pass filter circuit 20 for separate changes of the output caused by surface defects S of the LVD 4, a binary-signal generating circuit 21, a low pass filter circuit 22, and an amplifier 23. The low pass filter 22 picks up low-frequency components from the waveform-shaped output sent thereto from the sample hold circuit 19. The binary signal generating circuit 21 converts the output from the band pass filter circuit 20 by reference to a threshold signal provided by the amplifier 23.

To inspect the surface of the LVD 4, the LVD 4 is mounted on the disk drive 17 and driven at a constant, but relatively low, speed of rotation. It is preferred to oscillate the laser beam 3 at a constant speed greater than the seed of rotation of the LVD 4 so as to perform a precise scanning.

Figure 7:
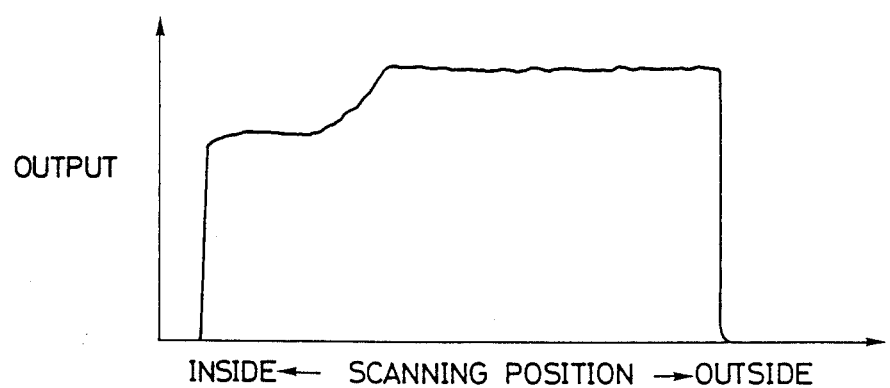
FIG. 7 is a graph, similar to FIG. 4, showing a waveform of a photoelectric output from a light-detecting unit receiving light reflected by the surface of an LVD with no surface defect, in accordance with the present invention.

Within a single line scanning of the surface of the LVD 4 along a line 5 with the laser beam 3, the light 3a reflected along line 5 from a smooth surface without defects travels past the light-detecting unit 7 without entering the same. It is preferred to provide a light-absorbing member (not shown) for absorbing the reflected light 3a that passes unit 7, so as to prevent the same from being reflected back toward the light-detecting unit 7. The laser beam 3 partly passes through the transparent protective layer 8 and reaches the signal recording surface of the LVD 4 where pits are formed. The light 11 diffracted and diffused by a pit travels to the light-detecting unit 7 and forms a circular-arcuate light pattern on the light-detecting unit 7 similar to the shape of the pit. Because the scanning line 5 is parallel to but spaced from the line 15 radial to the axis 6 of rotation of the LVD 4 by the distance L, a circular-arcuate light pattern of the diffused light 11 from a pit inclines on the light-detecting unit 7 at an angle with respect to that from an adjacent pit located outside the pit. Accordingly, the diffused light 11 from almost all of the pits on a single scanning line can be received by the light-detecting unit 7 having an effective light-receiving surface of a width of W. If not surface defects are on the single scanning line, the light-detecting unit 7 produces the output shown in FIG. 7, which is considered to indicate no significant flaws.

Figure 8A:
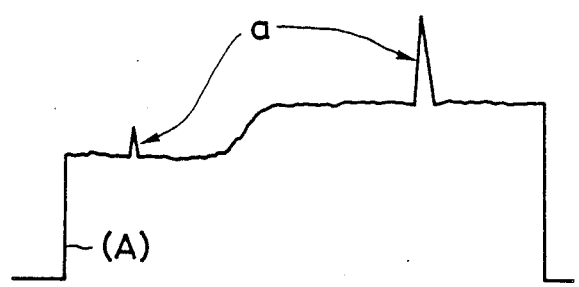
FIGS. 8A to 8C are outputs from various circuit elements of the surface inspection apparatus shown in FIG. 5.
Figure 8B:
Figure 8C:

If the light-detecting unit 7 receives diffused light from surface defects S of the LVD 4 within a single line scanning, it produces output (A) shown in FIG. 8A. The output (A) contains peaks which are due to the surface defects S. The output (A) is waveform-shaped by means of the sample hold circuit 19 and the band pass filter circuit 20 to the output (B) shown in FIG. 8B. On the other hand, the low pass filter 22 picks up low-frequency components, such as so-called "surge", from the output (A) from the sample hold circuit 19. The low-frequency components thus picked up are amplified by the amplifier 23 so as to provide an output (C) having a waveform shown in FIG. 8C. The output (C) is used as a signal defining a threshold level in the binary signal generating circuit 21. That is, the binary signal generating circuit 21 provides a binary signal of "1" indicating the presence of a surface defect when the output (B) exceeds the threshold level. Therefore, the binary signal generating circuit 21 provides an output (D) including pulse-like signals shown in FIG. 8C for the single line scanning. As will be apparent from the above, a surface defect which is located near the innermost track can be exactly detected.

Although the present invention has been fully described by way of the preferred embodiment thereof with reference to the accompanying drawings, it is to be noted that various changes and modifications will be apparent to those skilled in the art. Therefore, unless otherwise these changes and modifications depart from the scope of the present invention, they should be construed as included therein.

What is claimed is:

1. A method of scanning a surface of a disk having signal recording pits or bumps covered with a transparent layer, with a flying spot to detect surface defects of the disk surface, said method comprising:
    rotating said disk at a constant speed of rotation;
    scanning said disk surface along a scanning line parallel to but spaced from a line radial to the center of rotation of said disk; and
    receiving diffused light reflected by said disk surface to provide output corresponding to the intensity of said diffused light.

2. A method as defined in claim 1, wherein said scanning line is separated at least 10mm from said radial line.

3. A method as defined in claim 1, wherein said disk is a laser visual disk.

4. A disk surface inspection device which scans a surface of a disk having signal recording pits or bumps covered with a transparent layer, with a flying spot and detects flaws in the surface based on light reflected from the scanned surface, said disk surface inspecting device comprising:
    a disk drive for rotating said disk at a constant speed of rotation;
    a scanner for scanning a surface of said disk in rotation, along a scanning line parallel to but spaced from a line radial to the center of rotation of said disk;
    light-detecting means for receiving diffused light reflected by said disk surface to provide an electric output corresponding to the intensity of said diffused light;
    means for establishing a level for inspection according to fluctuation of a low-frequency component of said electric output; and
    detecting means for comparing said electric output with said level so as to detect abnormal components in said electric output, thereby detecting the presence of surface defects.

* * * * *